US00PP28769P2

(12) United States Plant Patent
Korlipara

(10) Patent No.: US PP28,769 P2
(45) Date of Patent: Dec. 12, 2017

(54) ***ECHINACEA* PLANT NAMED 'TNECHKIO'**

(50) Latin Name: ***Echinacea* spp.**
Varietal Denomination: TNECHKIO

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 14 days.

(21) Appl. No.: 14/999,887

(22) Filed: Jul. 14, 2016

(51) Int. Cl.
*A01H 5/02* (2006.01)

(52) U.S. Cl.
USPC ..... Plt./428

(58) Field of Classification Search
USPC ..... Plt./263.1, 428
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A new and distinct *Echinacea* plant named 'TNECHKIO' characterized by an amazing number of large inflorescences starting in the first season, very long bloom time with excellent rebloom, a very upright, very compact habit, bright orange ray florets surrounding dark cones, ray florets held horizontally, numerous, strong upright stems, and excellent vigor.

1 Drawing Sheet

Botanical denomination: *Echinacea* spp.
Variety designation: 'TNECHKIO'.

BACKGROUND OF THE INVENTION

The present invention relates to a new and distinct cultivar of *Echinacea* and given the cultivar name 'TNECHKIO'. *Echinacea* is in the family Asteraceae. The new cultivar is part of a planned breeding program for a container and edging series with compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Dixie Blaze' (U.S. Plant Pat. No. 26,109), the new cultivar is shorter and has more intensely colored ray florets.

This new *Echinacea* cultivar is uniquely distinguished by:

1. an amazing number of large inflorescences starting in the first season,
2. very long bloom time with excellent rebloom,
3. very upright, very compact habit,
4. bright orange ray florets surrounding dark cones,
5. ray florets held horizontally,
6. strong upright stems, and
7. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a nine-month-old *Echinacea* 'TNECHKIO' growing in the trial field in full sun in late July in Canby, Oreg.

DETAILED PLANT DESCRIPTION

The following is a detailed description of the new *Echinacea* cultivar based on observations of 9-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The *Royal Horticultural Society Colour Chart,* 5$^{th}$ edition.

Plant:

*Type.*—Herbaceous perennial.
*Hardiness.*—USDA Zones 4 to 9.
*Size.*—Grows to 33 cm wide and 31 cm tall to top of inflorescences.
*Form.*—Basal clump, with 8 to 9 stems from the base.
*Vigor.*—Excellent.
*Roots.*—Fibrous, with many downward growing and few laterals, ivory in color, Yellow White 158D, roots develop easily from cuttings from the crown.

Leaf (basal):

*Type.*—Simple.
*Shape.*—Lanceolate.
*Arrangement.*—Rosette.
*Blade size.*—Grows to 18 cm long and 7 cm wide.
*Margins.*—Entire.

*Apex*.—Acuminate.
*Base*.—Attenuate.
*Surface texture*.—Strigose on both sides.
*Venation*.—Pinnate, Yellow Green 145D on both sides.
*Color*.—Topside Green N137A, bottom side closest to Yellow Green 147A.
*Petiole description*.—Clasping, grows to 12 cm long and 4 mm wide, scabrous, narrow leafy edges, topside Yellow Green 147C with Red Purple 61A at base, bottom side closest to Yellow Green 147C tinted Red Purple 61A at base.

Leaf (stem):
*Type*.—Simple.
*Shape*.—Lanceolate.
*Arrangement*.—Alternate.
*Blade size*.—Grows to 14.5 cm long and 4 cm wide.
*Margins*.—Mostly entire.
*Apex*.—Acuminate.
*Base*.—Attenuate.
*Surface texture*.—Strigose on both sides.
*Venation*.—Pinnate, Yellow Green 145C on both sides.
*Color*.—Topside Green N137A, bottom side closest to Yellow Green 147A.
*Petiole description*.—Clasping, grows to 4.5 cm long and 4 mm wide, scabrous, narrow leafy edges, topside Yellow Green 147C, bottom side Yellow Green 147C.

Inflorescence:
*Type*.—Composite on terminal stalked heads.
*Flowering stem*.—Grows to 25.5 cm tall from the base of the plant to the terminal inflorescence; unbranched to branched, with 1 to 22 inflorescences per stem; diameter growing to 10 mm wide near the inflorescence; strigose; Yellow Green 147B in shade, tinted 187A in sun.
*Size*.—Grows to 11 cm wide and 5 cm deep as disc enlarges.
*Form*.—Ray florets held horizontally, reflexing somewhat in very old flowers, mature disc is conic.
*Immature inflorescence* (*bud*).—3 cm wide and 3 cm deep, ray florets held upright at a 70 degrees angle from vertical and rolled up so only the back color shows, Greyed Purple 189A except tip Greyed Yellow 160B, disc color Greyed Orange 165A except the center where Yellow Green 146B.
*Ray florets*.—Without pistil or stamen, about 20 in number, grow to 45 mm long and 15 mm wide, oblanceolate with the tip two-to-three-toothed (each acute), entire margins, base attenuate, glabrous on both sides; fully open florets topside closest to Orange Red 34A, bottom side Greyed Red 185D; florets fade gradually from tip down to topside Orange 26A.
*Disc*.—Flat becoming conic, becoming 40 mm deep and 40 mm wide with maturity, Greyed Purple 187A in background with bracts Orange 26A with tips Greyed Purple 187A.
*Disc florets*.—About 350 in number, each with 1 pistil and 4 stamen, grow to 10 mm long and 2 mm wide, each with one persistent, very stiff linear bract (16 mm long with the top 1 mm Greyed Purple 187A to 2 mm Orange 28C to 1 mm Greyed Purple 187A to Yellow Green 146B blending to White NN155A on bottom); corolla 6 mm long and 2 mm wide, tubular, 5 lobed, glabrous and glossy, Yellow Green 152B at the base blending to Greyed Purple 187A on lobes; pistil 11 mm long, ovary 4 mm long, White NN155D with top Yellow Green 144A, style 6 mm long White NN155A, 2-branched stigma spreading 3 mm wide, Greyed Purple 187A; stamen 4.5 mm long, filaments 2 mm long and White NN155B, anthers 2 mm long and Yellow Green 152B, pollen Yellow 20A.
*Involucral bracts*.—In 4 leafy series, area grows to 38 mm wide and 17 mm deep, lobes lanceolate in shape, reflexed, grow to 14 mm long and 4 mm wide, Green 137A, margins strigose, tip acute, strigose on both sides.
*Receptacle*.—Grows to 15 mm wide and 23 mm deep, White NN155B.
*Bloom period*.—June through October in Canby, Oreg.
*Fragrance*.—Slight.
*Lastingness*.—Each inflorescence lasts about two weeks in Canby, Oreg.

Seeds: 3 mm long and 2.5 mm wide, oval, Brown 200C.
*Fertility* .—Poor.

Disease and pests: No pests or diseases have been observed on plants grown under commercial conditions in Canby, Oreg. No resistances are known.

I claim:

1. A new and distinct *Echinacea* plant as herein illustrated and described.

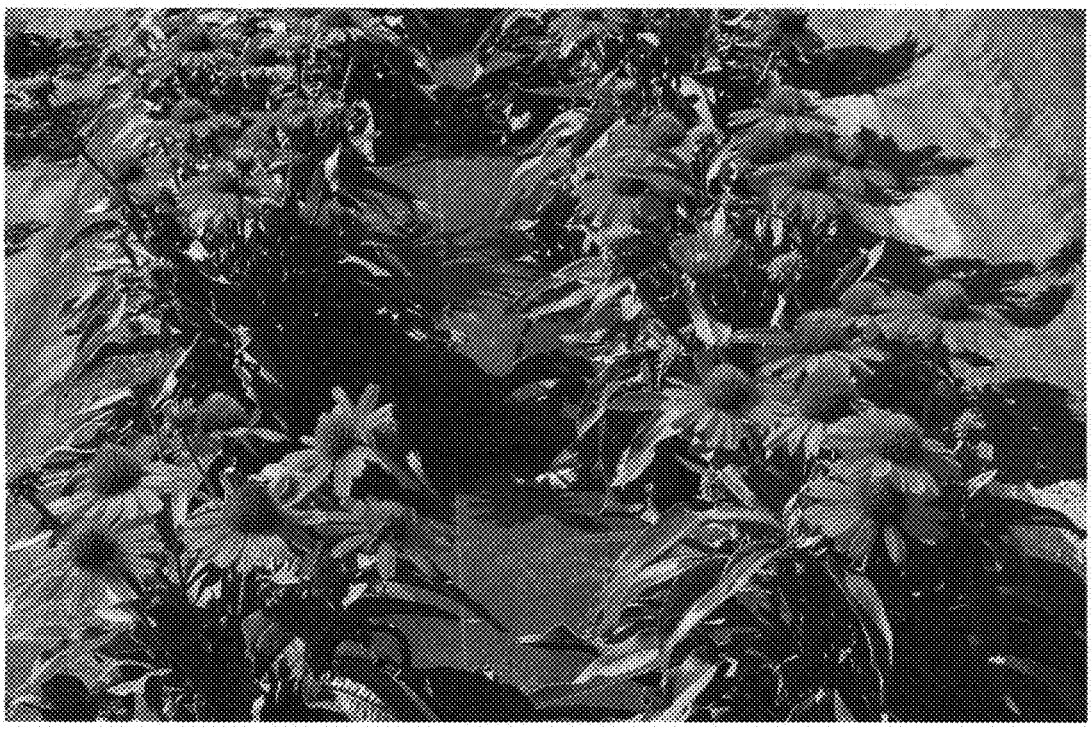

* * * * *